(12) United States Patent
Penny et al.

(10) Patent No.: US 7,785,322 B2
(45) Date of Patent: Aug. 31, 2010

(54) TISSUE TREATMENT SYSTEM

(75) Inventors: Keith Penny, Monmouth (GB); Nigel Mark Goble, Hungerford (GB); Colin Charles Owen Goble, Henley-on-Thames (GB)

(73) Assignee: Plasmogen Inc., New York, NY (US)

( * ) Notice: Subject to any disclaimer, the term of this patent is extended or adjusted under 35 U.S.C. 154(b) by 1171 days.

(21) Appl. No.: 11/354,880

(22) Filed: Feb. 16, 2006

(65) Prior Publication Data

US 2006/0189974 A1    Aug. 24, 2006

Related U.S. Application Data

(63) Continuation-in-part of application No. 10/792,765, filed on Mar. 5, 2004, now Pat. No. 7,335,199, which is a continuation-in-part of application No. 09/789,550, filed on Feb. 22, 2001, now Pat. No. 6,723,091.

(60) Provisional application No. 60/653,480, filed on Feb. 17, 2005, provisional application No. 60/183,785, filed on Feb. 22, 2000.

(51) Int. Cl.
    *A61B 18/18* (2006.01)
(52) U.S. Cl. .......................................... 606/34; 606/41
(58) Field of Classification Search .............. 606/32–52
    See application file for complete search history.

(56) References Cited

U.S. PATENT DOCUMENTS 2,909,735 A    10/1959    Hessler, Jr.

(Continued)

FOREIGN PATENT DOCUMENTS

DE    35 21 616 A1    12/1986

(Continued)

OTHER PUBLICATIONS

U.S. Appl. No. 11/281,594, filed Nov. 18, 2005, Goble et al.

(Continued)

*Primary Examiner*—Linda C Dvorak
*Assistant Examiner*—Benjamin Lee
(74) *Attorney, Agent, or Firm*—Oliff & Berridge, PLC (57) ABSTRACT

A tissue treatment system has a radio frequency generator and a handheld treatment instrument that generates a gas plasma jet for delivering thermal energy to a tissue surface to be treated. Incorporated in the housing for the generator is a calibration device for adjusting the energy output of the generator, if necessary, at the beginning of a treatment session. The calibration device has a target element with a target surface, a transducer for sensing changes in temperature of the target element with respect to the temperature of a reference element, and an energy output adjuster for adjusting the radio frequency energy output of the generator in response to a calibration signal generated by the transducer. The generator housing has a receptacle for locating the nozzle of the handheld instrument in juxtaposition with the target element so that when a plasma burst is generated as part of a calibration sequence it is incident on the target surface. The generator output is automatically adjusted to compensate for any deviation of a calibration value, produced from the calibration signal, from a reference value. Also disclosed is a method of regenerating the reticular architecture of tissue, the method including calibrating the energy delivery of a tissue treatment system.

19 Claims, 10 Drawing Sheets

U.S. PATENT DOCUMENTS

| | | |
|---|---|---|
| 3,280,362 A | 10/1966 | Ohtomo |
| 3,699,967 A | 10/1972 | Anderson |
| 3,838,242 A | 9/1974 | Goucher |
| 3,903,891 A | 9/1975 | Brayshaw |
| 4,040,426 A | 8/1977 | Morrison, Jr. |
| 4,781,175 A | 11/1988 | McGreevy et al. |
| 4,839,492 A | 6/1989 | Bouchier et al. |
| 4,901,719 A | 2/1990 | Trenconsky et al. |
| 5,364,392 A | 11/1994 | Warner et al. |
| 5,669,904 A | 9/1997 | Platt, Jr. et al. |
| 5,669,907 A | 9/1997 | Platt, Jr. et al. |
| 5,697,281 A | 12/1997 | Eggers et al. |
| 5,742,718 A | 4/1998 | Harman et al. |
| 5,755,753 A | 5/1998 | Knowlton |
| 5,843,019 A | 12/1998 | Eggers et al. |
| 5,888,198 A | 3/1999 | Eggers et al. |
| 5,948,011 A | 9/1999 | Knowlton |
| 5,968,034 A | 10/1999 | Fullmer et al. |
| 6,024,733 A | 2/2000 | Eggers et al. |
| 6,026,331 A * | 2/2000 | Feldberg et al. ............ 607/102 |
| 6,053,172 A | 4/2000 | Hovda et al. |
| 6,063,084 A | 5/2000 | Farin |
| 6,099,523 A | 8/2000 | Kim et al. |
| 6,135,998 A | 10/2000 | Palanker |
| 6,149,620 A | 11/2000 | Baker et al. |
| 6,159,194 A | 12/2000 | Eggers et al. |
| 6,190,381 B1 | 2/2001 | Olsen et al. |
| 6,210,402 B1 | 4/2001 | Olsen et al. |
| 6,213,999 B1 | 4/2001 | Platt, Jr. et al. |
| 6,228,078 B1 | 5/2001 | Eggers et al. |
| 6,296,636 B1 | 10/2001 | Cheng et al. |
| 6,309,387 B1 | 10/2001 | Eggers et al. |
| 6,387,092 B1 | 5/2002 | Burnside et al. |
| 6,413,253 B1 | 7/2002 | Koop et al. |
| 6,443,948 B1 | 9/2002 | Suslov |
| 6,464,681 B1 | 10/2002 | Heuser |
| 6,475,215 B1 | 11/2002 | Tanrisever |
| 6,518,538 B2 | 2/2003 | Bernabei |
| 6,565,558 B1 | 5/2003 | Lindenmeier et al. |
| 6,582,427 B1 | 6/2003 | Goble et al. |
| 6,629,974 B2 | 10/2003 | Penny et al. |
| 6,723,091 B2 | 4/2004 | Goble et al. |
| 6,920,312 B1 | 7/2005 | Benjamin |
| 2001/0034519 A1 | 10/2001 | Goble et al. |
| 2002/0043520 A1 | 4/2002 | Bernabei |
| 2002/0161362 A1 * | 10/2002 | Penny et al. ................ 606/41 |
| 2003/0069576 A1 | 4/2003 | Tanrisever |
| 2003/0125727 A1 | 7/2003 | Truckai |
| 2004/0044342 A1 | 3/2004 | Mackay |
| 2004/0186470 A1 | 9/2004 | Goble et al. |
| 2005/0149012 A1 | 7/2005 | Penny et al. |
| 2005/0256519 A1 | 11/2005 | Goble et al. |

FOREIGN PATENT DOCUMENTS

| | | |
|---|---|---|
| EP | 0 353 178 | 1/1990 |
| EP | 0 680 771 A1 | 11/1995 |
| EP | 0 787 465 A1 | 8/1997 |
| FR | 2 699 785 | 6/1994 |
| JP | A-09-299379 | 11/1997 |
| JP | A-09-299380 | 11/1997 |
| JP | A-10-024048 | 1/1998 |
| JP | A-10-024050 | 1/1998 |
| JP | A-10-286316 | 10/1998 |
| RU | 2138213 C1 | 9/1999 |
| WO | WO 89/07921 | 9/1989 |
| WO | WO 95/00759 | 1/1995 |
| WO | WO 95/24111 | 9/1995 |
| WO | WO 95/26686 | 10/1995 |
| WO | WO 98/35618 | 8/1998 |
| WO | WO 00/32127 | 6/2000 |
| WO | WO 00/53112 | 9/2000 |
| WO | WO 0162169 | 8/2001 |

OTHER PUBLICATIONS

Pelah I. et al., "Differential calorimeter for measurement of absorbed energy in laser-produced plasmas", Review of Scientific Instruments USA, vol. 48, No. 8, Aug. 1977, pp. 1068-1071.

Kulik P. et al., "Method for Measurement of Thermal-Flux Distribution in Low-Temperature Plasma", Instruments and Experimental Techniques, Consultants Bureau, New York, vol. 31, No. 2, Part 2, Mar. 1, 1988, pp. 410-412.

* cited by examiner

Day 0 following treatment at 3.5J

Day 4 following treatment at 3.5J

FIG. 12

Day 10 following treatment at 3.5J

TISSUE TREATMENT SYSTEM

This application claims priority of U.S. Provisional Patent Application No. 60/653,480, filed Feb. 17, 2005. This application is a Continuation-in-Part of U.S. patent application Ser. No. 10/792,765, filed Mar. 5, 2004 that is a Continuation-in-Part Application of U.S. patent application Ser. No. 09/789,550, filed Feb. 22, 2001, that in turn claims the benefit of priority of U.S. Provisional Patent Application No. 60/183,785, filed Feb. 22, 2000. The complete disclosures of U.S. Provisional Patent Application No. 60/653,480, U.S. patent application Ser. No. 10/792,765, U.S. patent application Ser. No. 09/789,550, and U.S. Provisional Patent Application No. 60/183,785, including the specification, drawings, and claims are incorporated herein by reference in their entirety.

BACKGROUND OF THE INVENTION

Field of the Invention

This invention relates to a tissue treatment system including a radio frequency (r.f.) generator and a treatment instrument connectible to the generator and to a source of ionisable gas for producing a plasma jet. The primary use of the system is skin resurfacing. The invention also relates to a method of regenerating the reticular architecture of the dermis.

CROSS REFERENCE TO RELATED PATENTS

A tissue treatment system is disclosed in U.S. Pat. Nos. 6,723,091 filed Feb. 22, 2001, and 6,629,974 filed Feb. 13, 2002 and U.S. patent application Ser. No. 10/727,765 filed Mar. 5, 2004. The complete disclosure of each of these patents and the application is incorporated in this application by reference.

SUMMARY OF THE INVENTION

In the system disclosed in the above patent and applications, a handheld treatment instrument has a gas conduit terminating in a plasma exit nozzle. There is an electrode associated with the conduit, and this electrode is coupled to a separate r.f. power generator which is arranged to deliver r.f. power to the electrode for creating a plasma from gas fed through the conduit. The delivered radio frequency power is typically at UHF frequencies in the region of 2.45 GHz and the instrument includes a structure resonant in that frequency region in order to provide an electric field concentration in the conduit for striking the plasma upstream of the exit nozzle, the plasma forming a jet which emerges from the nozzle and which can be used to effect local heating of a tissue surface.

The clinical effect of a system that delivers pulsed energy to the tissue of a patient is dependent on the amount of energy delivered, more particularly the instantaneous power integrated over the time of activation. It is, therefore, important to be able to confirm that the energy delivered by the system corresponds to the setting of the generator (which may be set by the user) and is within the specification of the system.

Typically, the power generated is monitored at one or more points and is compared with an expected value or range of values. In a closed-loop control system, feedback is used to adjust the generation of power. In an open-loop control system, deviation of one or more electrical parameters associated with the generator output from respective expected values by more than a certain degree may result in an error or fault indication, or in halt of the treatment by a control system forming part of the generator.

It is an object of the invention to provide an improved means of controlling treatment energy.

According to a first aspect of this invention, a tissue treatment system includes a radio frequency (r.f.) generator, a treatment instrument connectible to the generator and to a source of ionisable gas and operable to produce a plasma jet at a nozzle of the instrument when supplied with the ionisable gas and energised by the generator, and a calibration device which comprises: a target element having a target surface area, a transducer arranged to produce an electrical signal indicative of a temperature change of the target element within the target surface area, and a locating feature for locating the nozzle of the instrument in juxtaposition with the target surface area whereby, in operation of the instrument when in the receptacle, the plasma jet is incident upon the target surface area to cause the transducer to generate a calibration signal for adjusting the energy output of the generator.

In this way, the delivery of energy is calibrated with respect to delivery at the point of application so that the collective variation of components and processes in the generator, power supplies, and in transmission and connection paths is taken into account. Looked at it in a different way, the energy is calibrated in terms of the energy delivered at or beyond the distal end of a cable connecting the treatment instrument with the r.f. generator. Although the r.f. power produced by the generator may be monitored within the generator itself, it is possible, using means described above, to allow for imperfections in the connecting cable where significant power may be lost through heating. Cable degradation can occur through ageing or through other faults that introduce losses.

Even if r.f. power were to be measured at the distal end of the cable, calibrating energy delivered at the point of application allows adjustment to correct for, e.g., timing drift from the gas supply, gas supply leaks, degradation of an electrode within the treatment instrument, and degradation of the instrument nozzle or damage to the nozzle as a result of bad storage or handling.

In an alternative aspect, the invention may be seen as a means of calibrating the energy delivered to a simulated target by a gas plasma.

In a further aspect, means are provided for determining the energy delivered by a pulsed gas plasma using a measuring device, for instance a calorimeter which is integral to the plasma generating system and which may be electrically or otherwise connected to the generator so that the generator may be used to determine, indicate and/or control the plasma generation process.

The preferred system is a plasma skin resurfacing system which controls the damage and modification of superficial layers of a patient's skin. Such a clinical effect is achieved by rapidly heating the outer layers of the skin from the application of energy stored by ionising nitrogen gas. The plasma emerges from the nozzle of the treatment instrument which is typically held a few millimeters above the tissue surface to be treated.

In the preferred system in accordance with the invention, the calibration device has an output connected to the generator for coupling the calibration signal to the generator, and the generator includes an energy output adjuster allowing adjustment of the r.f. energy output of the generator in response to the calibration signal.

The adjuster may form part of a controller within the generator which is configured to perform an automatic calibration process. This process may comprise operating the generator to feed to the instrument a predetermined r.f. energy waveform, such as a series of bursts of r.f. energy lasting for a predetermined duration, to cause generation of a calibration plasma jet. This jet is directed at the target surface area of the calibration device, the calibration signal generated as a result of the calibration jet heating the target element being processed to obtain a calibration value which is compared with a reference value, so that the adjuster may be operated automatically in response to any deviation of the calibration value from the reference value by more than a predetermined degree in order to set the r.f. energy output for subsequent operation of the system in treating a patient's tissue. The calibration value is preferably a function of the combination of the levels of successive signal pulses which are generated by the transducer and which correspond to the plasma pulses.

Advantageously, the calibration device is in the form of a calorimeter incorporating a target element such as a metallic plate, a body portion underlying the metallic plate, and a temperature difference sensor, e.g., a Peltier device, located between the metallic plate and the calorimeter body portion. The sensor is arranged to produce an electrical output signal indicative of the difference in temperature between the metallic plate and the body portion.

In the preferred embodiment, the generator is contained within a floor-standing generator housing and the treatment instrument is coupled to the generator housing by a cable for conveying r.f. energy from the generator to the instrument. The calibration device may be mounted in or on the generator housing and has an associated instrument holder which can be used to hold the treatment instrument when not in use and, more particularly, receives the instrument for calibration, the instrument holder being shaped to locate the instrument longitudinally and transversely with respect to the target element. Indeed, the instrument and the instrument holder may have a corresponding asymmetrical cross-section in order that the rotational position of the instrument with respect to the calibration device is also defined.

According to another aspect of the invention, a method of calibrating a tissue treatment system comprises: placing the treatment instrument in a pre-defined location with respect to the target element; causing gas to be supplied to the instrument and simultaneously causing a burst of r.f. energy to be delivered to the instrument with a predetermined waveform and duration so as to generate a plasma jet incident upon the target element; automatically evaluating a calibration signal generated by the calibration device and representative of an output of the transducer resulting from heating of the target element by the plasma jet; and setting the r.f. energy output level of the generator according to the evaluation of the calibration signal.

Yet a further aspect of the invention is a calibration device for a gas plasma tissue treatment system, wherein the device comprises: a target element having a target surface area; a transducer arranged to produce an electrical signal indicative of a temperature change of the target element; and a receptacle for locating the nozzle of a handheld gas plasma generating instrument in juxtaposition with the target element, whereby in operation of the instrument when in the receptacle, the plasma jet is incident upon the target element to cause the transducer to generate a calibration signal indicative of the heating of the target element by the plasma jet.

Human skin has two principal layers: the epidermis, which is the outer layer and typically has a thickness of around 120μ in the region of the face, and the dermis which is typically 20-30 times thicker than the epidermis, and contains hair follicles, sebaceous glands, nerve endings and fine blood capillaries. By volume the dermis is made up predominantly of the protein collagen.

Ageing and exposure to ultraviolet (UV) light result in changes to the structure of the skin, these changes including a loss of elasticity, sagging, wrinkling and a pallor or yellowing of the skin consistent with reduced vascularity. The background to these effects is explained in our co-pending patent application entitled "Method of Regenerating the Reticular Architecture of the Dermis" filed on even date herewith, the disclosure of which is incorporated herein by reference.

According to a sixth aspect of the invention, a method of regenerating the reticular architecture of tissue using a tissue treatment system having a handheld tissue treatment instrument which emits a thermal energy beam comprises calibrating the energy delivery of the system by placing the treatment instrument in registry with a temperature-sensing target device, operating the system to direct a thermal energy beam at the target device, adjusting at least one energy setting of the system in response to an output of the target device to calibrate the system for energy output, moving the treatment instrument to a treatment position over an area of tissue to be treated, and operating the system to cause thermal energy to be delivered to the tissue surface using the calibrated system.

A seventh aspect of the invention comprises a method of regenerating the reticular architecture of tissue using a source of thermal energy comprising the steps of: calibrating the source by operating the source in conjunction with a delivered-energy-sensing target device and adjusting the source in response to an output of the device, and operating the adjusted source to form first and second adjacent regions of thermally modified tissue in the region of the DE junction, said first region overlying said second region and being thermally modified to a greater extent than said second region.

According to a further aspect of the invention, a method of regenerating the reticular architecture of the dermis using a source of thermal energy comprises the steps of: calibrating the source by operating the source in conjunction with a delivered-energy-sensing target device and adjusting the source in response to an output of the device, and operating the adjusted source and directing it at the surface of the skin to form first and second adjacent regions of thermally-modified tissue in the region of the epidermis and dermis of the skin, said first region overlying said second region and being thermally modified to an extent that it separates from said second region some days after the delivery of the thermal energy, and the depth of said separation being dependent on the amount of energy delivered and the thermal capacity of the skin.

In a preferred embodiment, the thermal energy source is operated for a single pass over the skin surface, the thermal energy source being arranged to have an energy setting dependent on the desired depth of effect. Alternatively, the thermal energy source is operated over at least two passes over the skin surface, the energy levels of the passes being chosen dependent on the desired depth of effect.

In either case, the energy setting of the thermal energy source may be such as to create vacuolation on the first pass. In the latter case, the energy setting of the thermal energy source may be such as not to create vacuolation on the first pass, thereby enabling a second pass without removing the treated skin.

Preferably, the energy setting of the thermal energy source is such as to preserve the integrity of the epidermis as a biological dressing.

In a preferred embodiment, the thermal energy source is operated so that a line of cleavage occurs within the skin 2 to 5 days following treatment, the line of cleavage occurring between said first and second regions. In one particular case, the operation of the thermal energy source may be such as to form a line of cleavage from 2 to 3 cells deep in the stratum corneum of the superficial epidermis and the upper dermis.

Advantageously, the operation of the thermal energy source is such that the tissue in the first region is sloughed tissue. In this case, the sloughed tissue is removed once a new epidermis has been substantially generated in the region of the line of cleavage.

Preferably, the tissue below the line of cleavage in said second region includes the lower epidermis, the basal membrane and the DE Junction. More preferably, at least the thermally-modified basal membrane and the DE Junction are regenerated.

In one particular case, the line of cleavage forms below areas of solar elastosis, such that the solar elastosis and deranged fibroblasts are sloughed.

Preferably, the operation of the thermal energy source is such as to denature dermal collagen in the second region.

In a preferred embodiment, the tissue in said second region undergoes a regenerative process following regeneration of the epidermis.

In this case, the reticular architecture of the dermis is regenerated in whole, or in part, by fibroblasts less exposed to the effects of UV radiation.

The collagen architecture and/or elastin architecture and/or the GAGS of the dermis is regenerated in whole, or in part, by fibroblasts less exposed to the effects of UV radiation.

Preferably, the healing process is such that risk of scarring and hypo pigmentation is substantially eliminated.

Advantageously, a progressive improvement in skin changes associated with ageing and photodamage occur over a period of between 6 and 12 months following treatment.

In a preferred embodiment, the source of thermal energy is an instrument having an electrode connected to a power output device, and wherein the power output device is operated to create an electric field in the region of the electrode; a flow of gas is directed through the electric field to generate, by virtue of the interaction of the electric field with the gas, a plasma; the plasma is directed onto the tissue for a predetermined period of time; and the power transferred into the plasma from the electric field is controlled so as to desiccate at least a portion of the dermis with vapour pockets formed in dermis cells.

Preferably, the power output device is operated to deliver discrete pulses of heat of millisecond duration.

Advantageously, the pulses have a duration in the range of from about 0.5 milliseconds or 2 milliseconds to about 100 milliseconds, and preferably a duration in the range of from about 4.5 to about 15.4 milliseconds.

Conveniently, the power output device is operated to deliver energy in the range of from about 1 Joule to about 4 Joules for an instrument having a first predetermined nozzle diameter, and to deliver energy in the range of from less than 0.5 Joules to about 2.0 Joules for an instrument having a second predetermined diameter that is less than the first predetermined diameter.

Preferably, the first predetermined diameter is substantially 5 mm and the second predetermined diameter is substantially 1.5 mm.

The thermal energy may be delivered to the tissue from a thermal energy source as a jet of fluid having stored heat energy at the tissue surface, the jet of fluid typically comprising a jet of ionised diatomic gas.

BRIEF DESCRIPTION OF THE DRAWINGS

The invention will be described below by way of example with reference to the drawings in which.

DETAILED DESCRIPTION OF THE PREFERRED EMBODIMENTS

Figure 1:
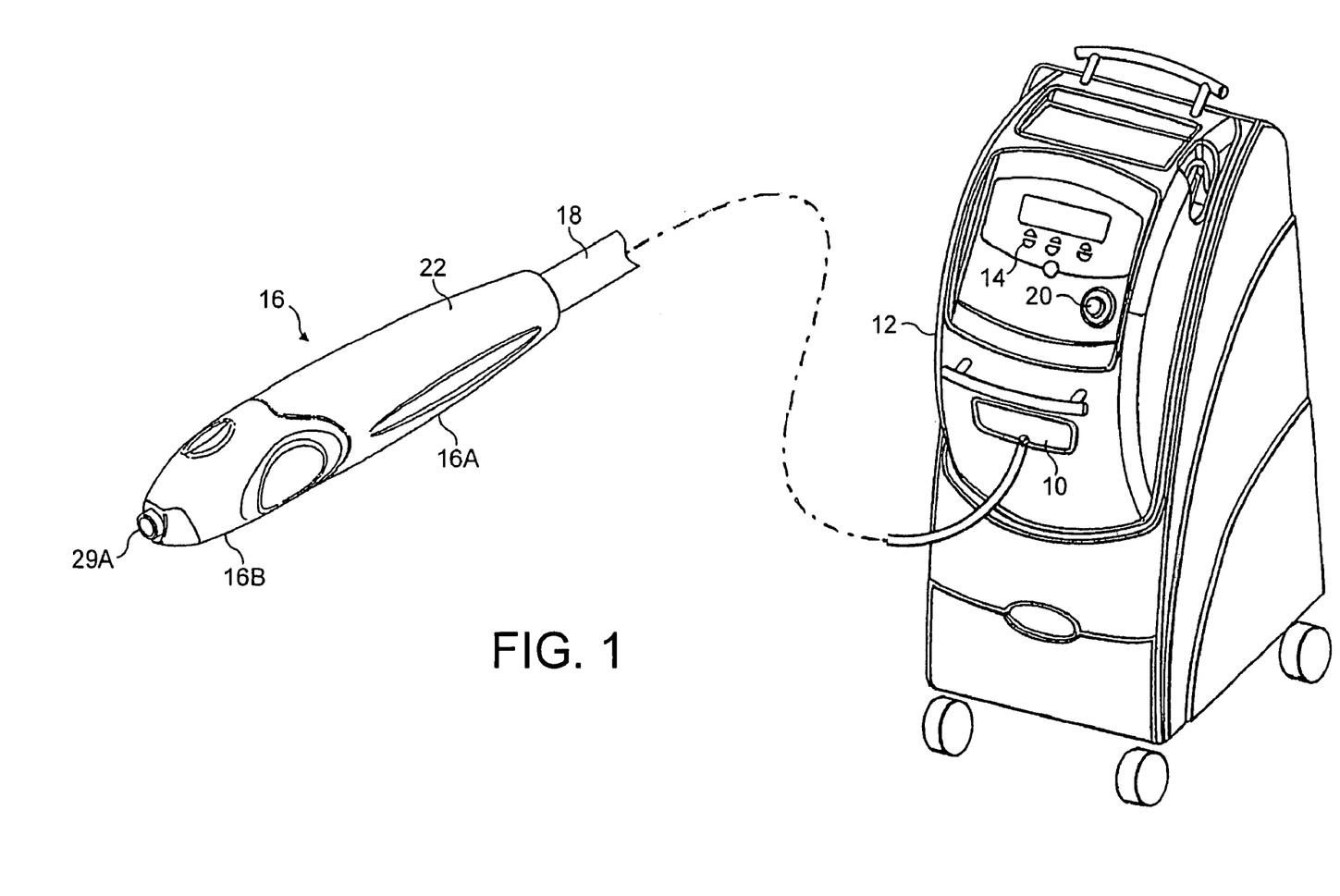
FIG. 1 is a diagrammatic view of a tissue treatment system in accordance with the invention.

Referring to FIG. 1, a tissue treatment system in accordance with the invention has a generator 10 mounted in a floor-standing generator housing 12 and having a user interface 14 for setting the generator to different energy level settings. A handheld tissue treatment instrument 16 is connected to the generator by means of a cord 18. The instrument 16 comprises a re-usable handpiece part 16A and a disposable nose assembly 16B.

The generator housing 12 has an instrument holder 20 for storing the instrument when not in use.

The cord 18 includes a coaxial cable for conveying r.f. energy from the generator 10 to the instrument 16, and a gas supply pipe for supplying nitrogen gas from a gas reservoir or source (not shown) inside the generator housing 12. At its distal end, the cord 18 passes into the casing 22 of the re-usable handpiece part 16A.

Figure 2:
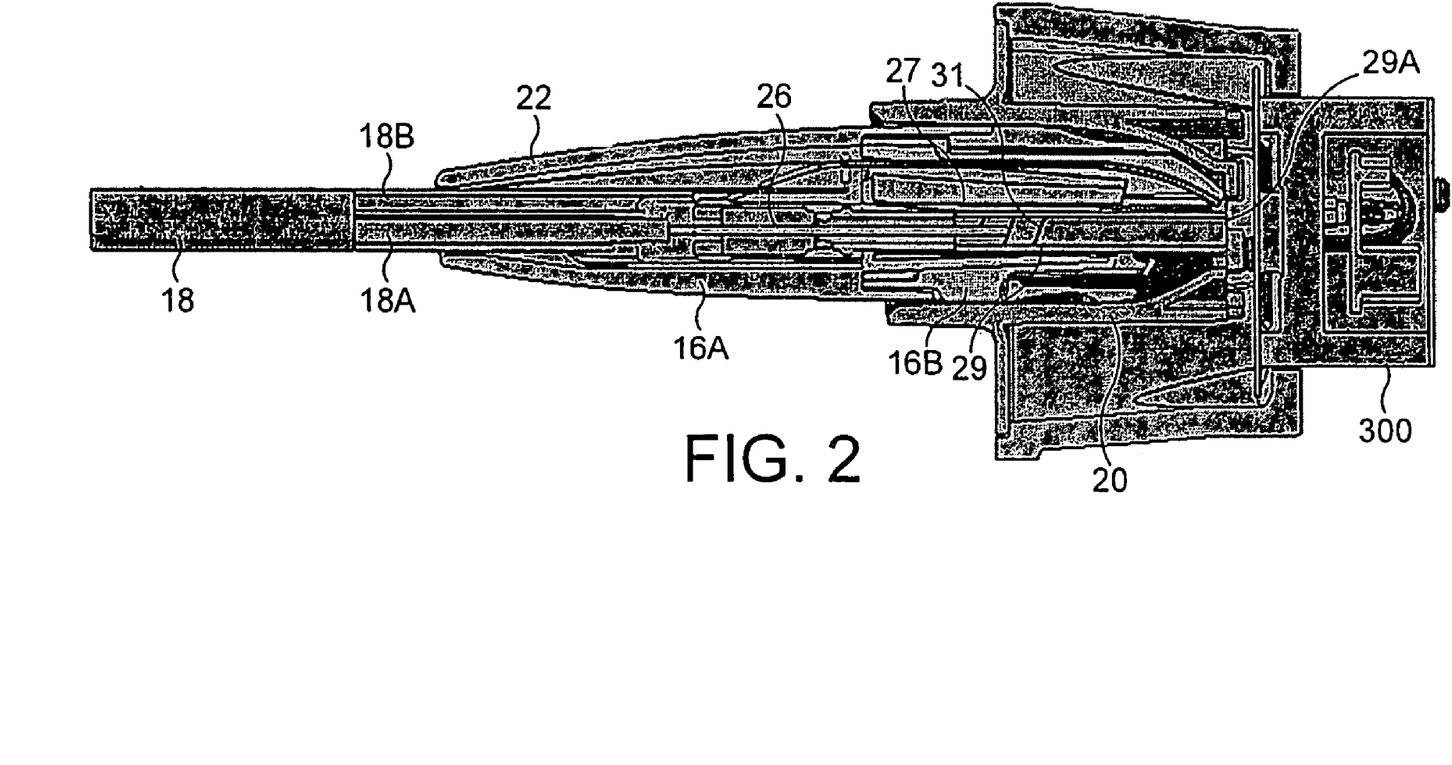
FIG. 2 is a longitudinal cross-section of a tissue treatment instrument forming part of the system of FIG. 1, housed in an instrument holder.

In the re-usable handpiece 16A, the coaxial cable 18A is connected to inner and outer electrodes 26 and 27, as shown in FIG. 2, thereby coupling the electrodes to the generator to receive r.f. power. The inner electrode 26 extends longitudinally within the outer electrode 27. Between them is a gas conduit in the form of a heat-resistant tube 29 (preferably made of quartz) housed in the disposable instrument nose assembly 16B. When the nose assembly 16B is secured to the reusable handpiece part 16A, the interior of the tube 29 is in communication with the gas supply pipe interior, the nose assembly being received within the reusable part such that the inner and outer electrodes 26, 27 are associated with the tube, the inner electrode 26 extending axially into the tube 21 and the outer electrode 27 extending around the outside of the tube 29.

A resonator in the form of a helically wound tungsten coil 31 is located within the quartz tube 29, the coil being positioned such that, when the disposable nose 16B is secured in position in the reusable portion of the handpiece, the proximal end of the coil is adjacent the distal end of the inner electrode 26. The coil is wound such that it is adjacent and in intimate contact with the inner surface of the quartz tube 29.

In use, nitrogen gas is fed by a supply pipe to the interior of the tube 29 where it reaches a location adjacent the distal end of the inner electrode 26. When an r.f. voltage is supplied via the coaxial cable to the electrodes 26 and 27 an intense r.f. electric field is created inside the tube 29 in the region of the distal end of the inner electrode. The field strength is aided by the helical coil which is resonant at the operating frequency of the generator and, in this way, conversion of the nitrogen gas into a plasma is promoted, the plasma exiting as a jet at a nozzle 29A of the quartz tube 29. The plasma jet is directed onto tissue to be treated, the nozzle 29A typically being held a few millimetres from the surface of the tissue.

Following repeated use of the instrument, the quartz tube 29 and its resonant coil 31 require replacement. The disposable nose assembly 16B containing these elements is easily attached and detached from the reusable part 16A of the instrument, the interface between the two components 16A, 16B of the instrument providing accurate location of the quartz tube 29 and the coil 31 with respect to the electrodes 26, 27.

Figure 3:
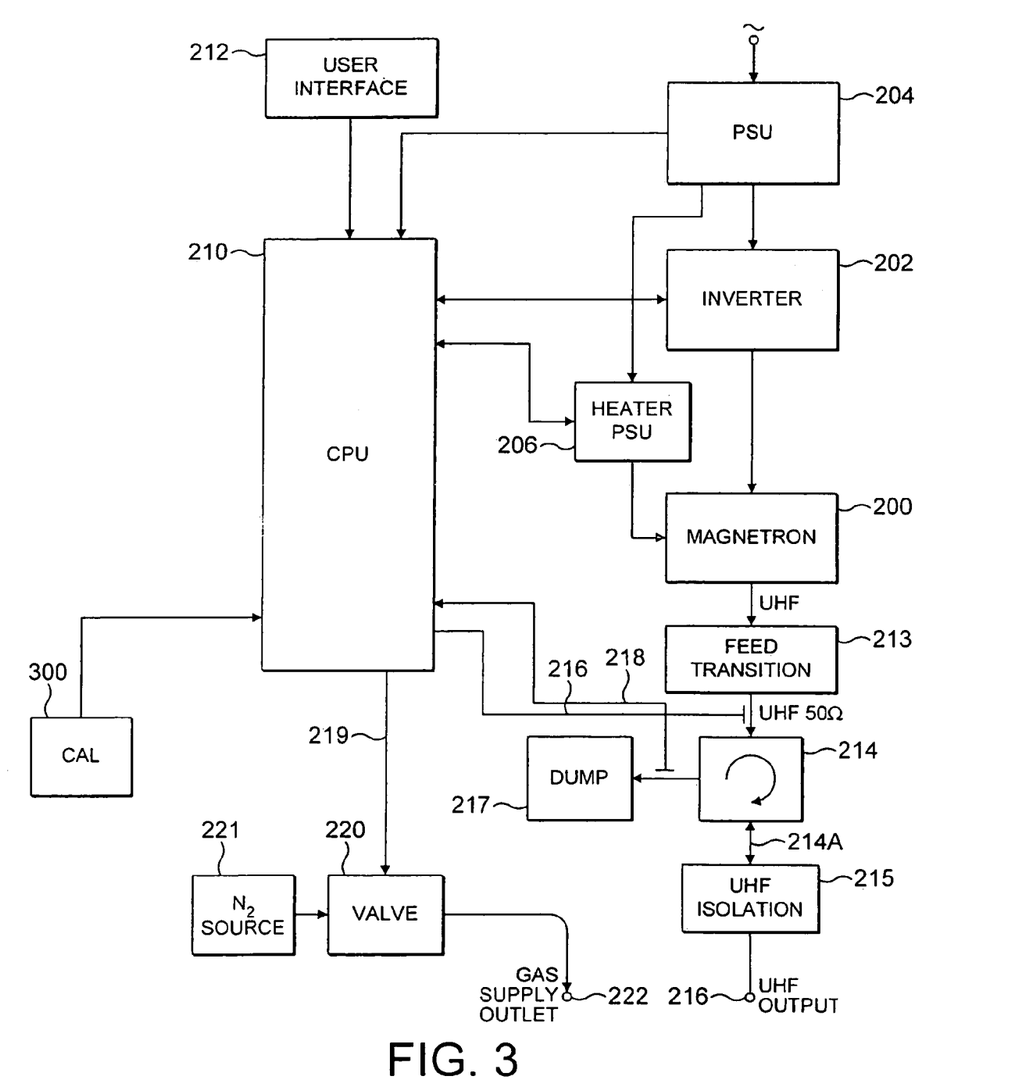
FIG. 3 is a block diagram of a radio frequency generator for use in the system of FIG. 1.

Referring to FIG. 3, r.f. energy is generated in a magnetron 200. Power for the magnetron 200 is supplied in two ways, firstly as a high DC voltage for the cathode, generated by an inverter 202 supplied from a power supply unit 204 and, secondly, as a filament supply for the cathode heater from a heater power supply unit 206. Both the high voltage supply represented by the inverter 202 and the filament supply 206 are coupled to a CPU controller 210 for controlling the power output of the magnetron. A user interface 212 is coupled to the controller 210 for the purpose of setting the power output mode, amongst other functions.

The magnetron 200 operates in the high UHF band, typically at 2.475 GHz, producing an output on an output line which feeds a feed transition stage 213 for converting the magnetron output to a coaxial 50 ohms feeder, low frequency AC isolation also being provided by this stage. Thereafter, a circulator 214 provides a constant 50 ohms load impedance for the output of the feed transition stage 213. Apart from a first port coupled to the transition stage 213, the circulator 214 has a second port 214A coupled to a UHF isolation stage 215 and hence to the output terminal 216 of the generator for delivering RF power to the handheld instrument 16 (FIG. 1). Reflected power is fed from the circulator 214 to a resistive power dump 215. Forward and reflected power sensing connections 216 and 218 provide sensing signals for the controller 210.

The controller 210 also applies via line 219 a control signal for opening and closing a gas supply valve 220 so that nitrogen gas is supplied from the source 221 to a gas supply outlet 222 from where it is fed through the gas supply pipe in the cord 18 to the instrument 16 (FIG. 1), when required.

The controller 210 is programmed to pulse the magnetron 200 so that, when the user presses a footswitch (not shown in the drawings), r.f. energy is delivered as a pulsed waveform to the UHF output 216, typically at a pulse repetition rate of between about 1 Hz and about 4 Hz. A single pulse mode is also provided. The pulses preferably have durations in the range of from 2 ms to 100 ms. The controller 210 also operates the valve 220 so that nitrogen gas is supplied to the handheld instrument simultaneously with the supply of r.f. energy. Further details of the modes of delivery of r.f. energy are set out in the above-mentioned U.S. Pat. No. 6,723,091.

Although r.f. power levels within the generator are monitored by the controller 210, various factors can affect the actual energy or power delivered to the tissue being treated by the plasma jet emerging from the instrument 16 (FIG. 1). Accordingly, the delivered energy or power may not correspond accurately to that set by the controller 210, whether according to internal settings programmed into the controller 210 or according to settings performed by the user using the user interface 212.

External factors affecting energy delivery include imperfections in the connecting cable due to, for instance, ageing or physical damage, variations in the gas supply, degradation of the inner electrode 26 (FIG. 2) of the handpiece, and degradation or damage to the quartz tube 29.

Figure 4:
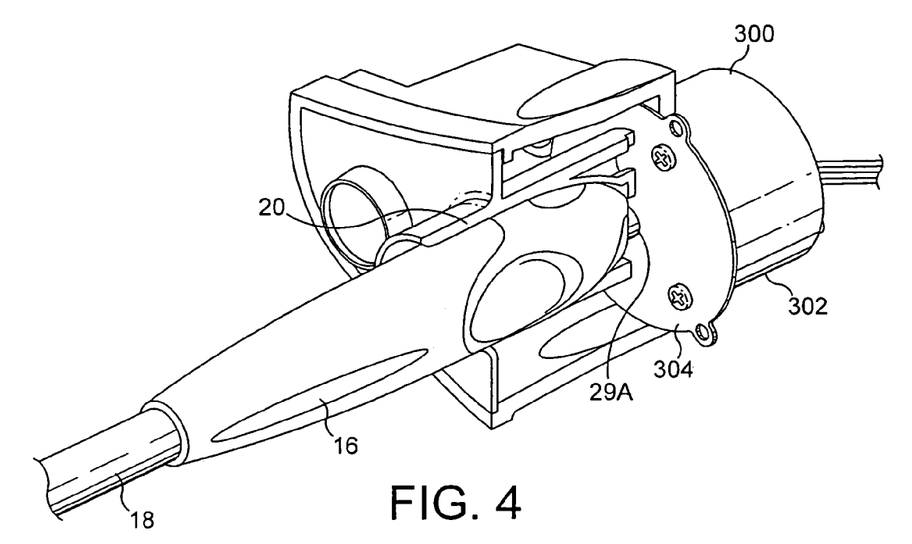
FIG. 4 is a cut-away view of the tissue treatment instrument and a calibration device of the system of FIG. 1, the instrument located in the instrument holder.
Figure 5:
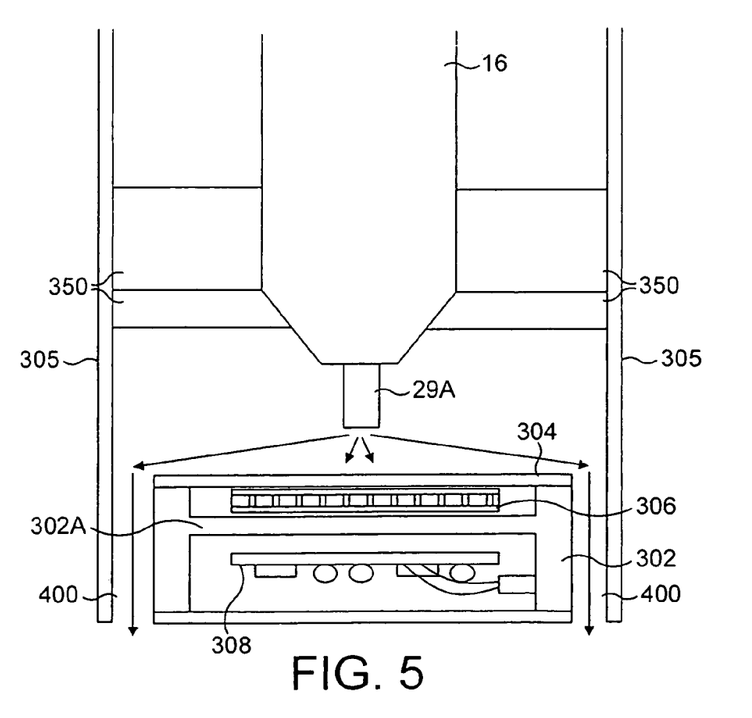
FIG. 5 is a diagrammatic representation of the tissue treatment instrument and the calibration device.
Figure 6:
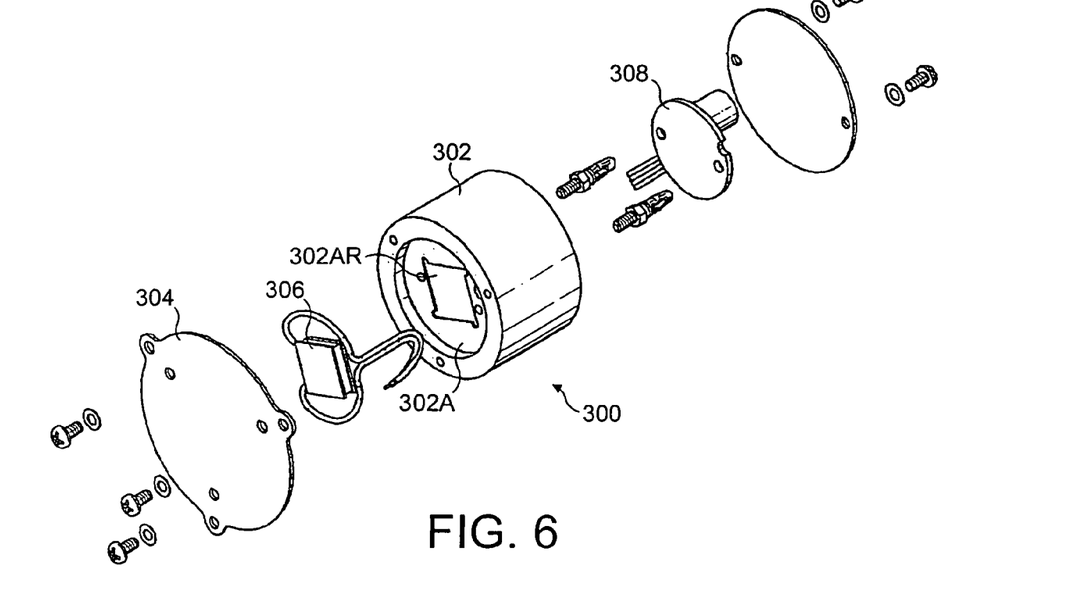
FIG. 6 is an exploded view of the calibration device.

To take account of these factors, the generator includes a calibration device 300, as shown in block form in the generator block diagram of FIG. 3 and in the views of FIGS. 4, 5 and 6.

The calibration device 300 is constituted by a cylindrical calorimeter having a cylindrical body 302 and a planar target element in the form of a thin aluminium plate 304 attached to an end face of the body 302. This calorimeter device 300 is mounted in the generator housing beneath the instrument holder 20, as shown in FIG. 4. The internal shape of the instrument holder 20 corresponds to the external shape of a distal portion of the handheld instrument or handpiece 16. In particular, the internal surfaces of the instrument holder 20 are tapered or stepped to locate the nose of the handpiece 16 longitudinally with respect to the target plate 304 of the calibration device 300. The instrument holder 20 is also shaped to locate the handpiece 16 laterally and rotationally, the handpiece distal portion having an asymmetric cross-section which co-operates with corresponding features of the interior of the instrument holder 20 when the handpiece is inserted into the holder. In this way, the position and orientation of the nozzle 29A and, especially, its spacing from the target plate 304 are accurately defined.

In FIG. 5, instrument locating features are illustrated diagrammatically as is the calibration device 300. When the instrument 16 is operated in a calibration routine, and when housed in the instrument holder 20, a plasma jet is directed from the nozzle 29A so as to be incident upon a predetermined target surface portion of the target plate 304. Exhausted gas flows radially outwardly from the target surface portion of the target plate which is in registry with the nozzle 29A to escape through circumferential vents 400 between the edge of the target plate 304 and components 305 of the generator housing.

As shown diagrammatically in FIG. 5 and in the exploded representation of FIG. 6, the calorimeter has an aluminium cylindrical body 302 with an internal heat sink wall 302A upon which is mounted a temperature transducer in the form of a Peltier device 306. A recess 302AR (FIG. 6) is formed in the calorimeter heat sink wall 302A for this purpose. The transducer 306 is sandwiched between the heat sink wall 302A and the target plate 304 and is in intimate contact with both. A thermally conductive compound is applied to improve thermal conductivity between the Peltier device 306 and the two surfaces with which it is in contact.

The instrument holder 20 positions the axis of the heat resistant tube 29 centrally with respect to the circular target plate 304 and perpendicularly with respect to the surface of the latter.

The Peltier device 306 has the property (the Seebeck effect) that when there is a difference in temperature between its two faces, a voltage is generated across the device. The voltage is linearly related to the temperature difference. The calibration device 300 includes within its body an electronic circuit 308 which conditions and amplifies the signal from the Peltier device to produce a calibration signal. The output from the circuit is connected to the controller 210 of the generator (see FIG. 3) so that the calibration signal can be evaluated. Preferably, the target plate 304 is grounded to the ground of the generator housing.

Operation of the calibration device will now be described with reference to FIG. 7.

When the plasma jet impinges on the target plate 304, the target plate is heated. Heat is conducted to the abutting surface of the Peltier device 306. Since the opposite surface of the Peltier device 306 is in thermal contact with the calorimeter body 302 which is at ambient or near-ambient temperature, a temperature differential is created between the two surfaces of the Peltier device 306. This results in a voltage on the output of the Peltier device. Since the temperature rise of the aluminium plate is substantially proportional to the energy delivered, the voltage output of the Peltier device is substantially proportional to delivered energy.

In principle, a single plasma pulse (produced by activating the nitrogen gas supply instrument 16 and simultaneously feeding a single pulse of r.f. energy to the instrument) can be used to characterise the energy delivered by the instrument. In practice, for greater accuracy, it is advantageous to record the effect of a series of plasma pulses and to produce a calibration signal which includes a corresponding plurality of samples of the Peltier device output signal. In the controller 210, a calibration value is computed which is a function of these calibration signal samples, for instance, by averaging to reduce the effects of noise. However, under these circumstances, with a succession of plasma pulses emitted over a period of time (e.g. between half a second and two seconds), the effectiveness of the wall 302A of the calorimeter body as a heat sink diminishes owing to the imperfect dissipation of heat by the calorimeter body 302. As an illustration, if the effect of thermally insulating the Peltier device from the heat sink wall 302A of the calorimeter body is considered, it will be appreciated that this reference surface of the Peltier device, i.e the surface opposite to that contacting the target plate 304, would be rapidly heated and would eventually become sufficiently hot that the temperature difference between the two surfaces is virtually zero. This would have the effect that the voltage rise with each plasma pulse would be progressively reduced. Even with the Peltier device 306 in intimate thermal contact with the calorimeter body wall 302A, this effect is observed to some extent and, indeed, is visible in the oscilloscope trace of FIG. 7.

Figure 7:
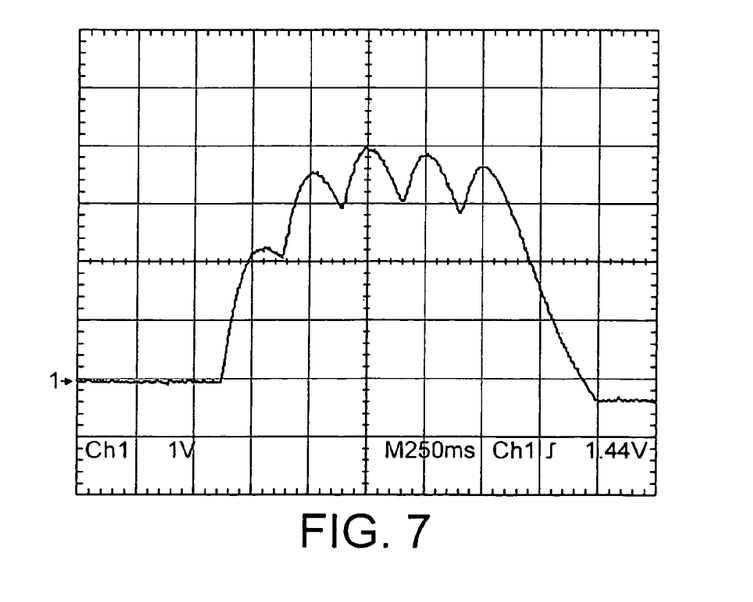
FIG. 7 is a diagram showing an oscilloscope trace of a transducer output signal.

Referring to FIG. 7, an exemplary voltage signal from the Peltier device is shown, being the output observed when five plasma pulses are fired at the target plate 304 from the instrument 16 in the instrument holder 20 (FIG. 4). The repetition rate of the pulses in this instance is about 4 Hz. The Peltier device output signal resulting from the first pulse of the pulse train appears on the left hand side of the oscilloscope display in FIG. 7. Although each plasma pulse delivers the same nominal amount of energy, it is seen that the corresponding signal peak for each pulse is different as a consequence of the progressive heating of the calorimeter body wall 302A (FIG. 6).

In this embodiment, the conditioning and amplifying circuit 308 is adjusted so that a plasma pulse equivalent to an energy pulse of 4 joules results in an output voltage change in the region of 1 to 10 volts. Voltages within this range are chosen to avoid electrical interference problems as far as possible. The scaling of voltage with respect to energy is otherwise largely arbitrary and is selected to suit the requirement of interfacing with the CPU of the controller 110 of the generator.

Since the difference in the voltage level for each of the five plasma pulses, as seen in FIG. 7, is a function of the thermal characteristics of the calorimeter, and for a given calorimeter design these thermal characteristics are fixed, once the response of the calorimeter to a plasma pulse of known energy is defined, the calorimeter can be used to measure energy delivered by the treatment instrument.

In one preferred embodiment, the controller 210 (FIG. 3) samples the peaks of the second, third and fourth Peltier device output pulses and processes these by averaging the peak levels, and compares the resulting value with a stored expected value. In an alternative preferred embodiment the peak level associated with the third output pulse is sampled.

Consistency of results is achieved because the instrument holder 20 shown in FIG. 4 avoids misalignment of the instrument 16 with respect to the target plate 304. Any misalignment may result in variation in the "stand-off" distance from the plasma exit nozzle 29A and the target plate 304, the radial offset of the plasma axis with respect to the centre of the Peltier device, and the axis not being perpendicular to the target plate.

Providing the instrument holder 20 is suitably shaped, the calibration device can be operated with the required performance and immunity to misalignment when used with different instruments having different exit nozzle diameters.

One feature that reduces the effect of any misalignment which may be the consequence of manufacturing tolerances or variations in the manner in which the instrument is inserted and positioned in the instrument holder, the Peltier device has a sensing area greater than the nominal width of the plasma jet from the instruments to be calibrated. In addition, the Peltier device has a distributed array of individual temperature sensing elements to reduce sensitivity to radial misalignment.

The relatively large area of the Peltier device 306 also increases the likelihood of the whole of the plasma jet impinging upon the target plate within the sensing area of the Peltier device. Therefore, given that the plasma jet is commonly not well collimated and diverges on exit from the nozzle 29A, the calibration device is relatively insensitive to variations in stand-off distance of the nozzle 29A from the target plate 304.

Likewise, the relatively large area of the Peltier device 306 contributes to immunity to variations in the alignment of the plasma jet axis with respect to the target plate 304.

The preferred embodiment of the system in accordance with the invention is configured to define a semi-automatic calibration procedure.

Prior to treatment, the user is required to fit the treatment instrument 16 into the instrument holder 20 (FIG. 4). In response to electrical sensing of correct fitment of the instrument in the holder 20 or in response to indication from the user, e.g. in the form of a key-press confirmation, a signal is provided to the user requesting operation of the footswitch to activate the instrument. Where the instrument has a disposable portion, the system may also require confirmation that this portion has been fitted.

Upon activation of the footswitch, the generator and automatic control of the CPU in the controller 210 (FIG. 3) causes the generation of the predetermined number (five) of plasma pulses at a specified interval between each consecutive pulse. In the preferred embodiment, the pulse repetition interval is 250 ms. The calibration signal from the calibration device is then processed by the controller 210 and the resulting calibration value compared with an expected value for the particular instrument in question (or particular nozzle where more than one type of nozzle may be fitted).

Depending on the size and nature of any deviation from the expected value, the generator may:

a) Make a small adjustment—'automatic calibration' or self calibration—to the r.f. power level to compensate for a small deviation (e.g., up to or less than 10% or otherwise compatible with the system as a whole meeting the safety and efficacy requirements of a medical device) from a nominal energy setting. This enables variations in the performance of the system and disposable nozzle to be compensated for automatically and gives greater accuracy in energy delivery than would otherwise be the case. Note that excessive output power adjustment can cause overdose or critical limiting circuitry that operates independently of the software control system to detect a fault condition and so prevent further operation.

b) Determine that ageing or other effects have degraded the generator and/or its accessories such that maintenance or another servicing function is likely to be required but that, otherwise, the output level can be sufficiently well compensated for such that the energy delivery accuracy is as required and consistent with the safety and efficacy of the system. This may be communicated to the user through a message or other indicator.

c) Determine that the nozzle or other system part that may be readily changed by the user is faulty and, on confirmation of replacement, cause the test to be repeated.

d) Determine that there is a fault caused, for example, by damage to the r.f. cable between the generator and handpiece, that will cause incorrect operation and incorrect delivery of energy to the patient. In this case the generator will halt further operation (unless reset, in which case the test must be performed before treatment). An appropriate message is then displayed to indicate the fault condition to the user.

With regard to the calibration and adjustment of the system, the principle steps performed by the controller 210 in combination with the calibration device 300 include adjusting the generator in response to a calibration measurement to compensate for a deviation in an expected energy measurement value, thereby establishing a new energy delivery setting for a treatment session which begins with the calibration procedure. In the preferred system, the energy level is adjusted substantially in proportion to the deviation of the measurement from the expected value. This may be performed up to the limit or limits of a predetermined adjustment range, e.g. 10% above and/or 10% below the expected value. In particular, the preferred system performs a sequence of steps as shown in the flow diagram of FIG. 8.

Figure 8:
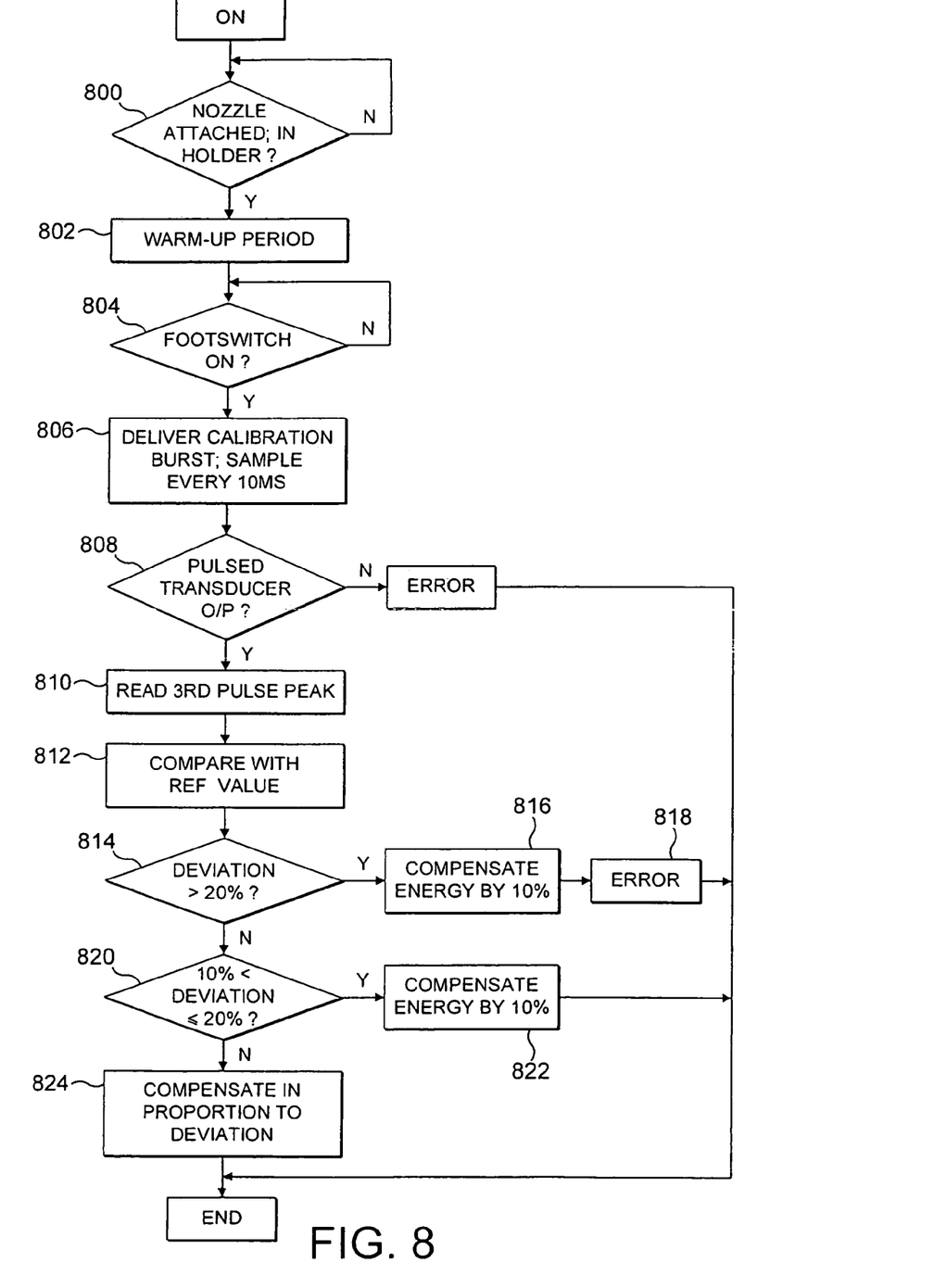
FIG. 8 is a flow diagram illustrating the principle of an energy level compensation method.

Referring to FIG. 8, an initial self-check step 800 involves the user confirming that the handpiece has a nozzle attached and that the handpiece and the nozzle have been placed in the instrument holder 20 (FIG. 1). After a warm-up period 802, the controller detects operation of the footswitch for at least a minimum predetermined time (step 804). A calibration energy burst is then delivered, the plasma jet impinging upon the target element, and the Peltier device output signal is sampled every 10 ms (step 806). Providing a pulsed output signal is detected (step 808), the peak level of a predetermined output signal pulse, in this case the third pulse, is measured (step 810) and compared with an expected or reference value (step 812).

If the comparison indicates a deviation of the output signal level greater than 20% from the expected value (step 814) the generator output is adjusted by 10% as a part-compensation (step 816), and an error indication provided (step 818).

If the deviation from the expected value is less than or equal to 20% (step 820), but greater than 10%, the generator output is adjusted by 10% (step 822) but no error signal is provided.

If the deviation is less than 10%, the energy level setting of the generator is adjusted in proportion to the deviation and in a direction so as to compensate for the deviation (step 824) (i.e. by increasing the generator output if the measured value is lower than the expected value or by decreasing the generator output if the measured value is higher than the expected value.

It will be appreciated, therefore, that in the preferred embodiment, energy level compensation is performed on a linear basis up to a predetermined maximum adjustment, in this case 10% in energy terms. Greater deviations of the measured value from the expected value give rise to a maximum energy level adjustment equal to the predetermined maximum adjustment, i.e. 10%, thereby part-compensating for the deviation.

As previously stated, it is a system requirement that the energy delivery be checked before patient treatment. The preferred embodiment allows the user to perform a calibration check at a later time.

In addition, on change of nozzle (either initiated by the user or through other means) the user is required by the generator to check the performance of the instrument.

In the preferred embodiment, a device having an array of semiconductor elements (the Peltier device) is used as a temperature sensing transducer. It is, as an alternative, also possible to use a thermocouple or an array of thermocouples, or one or more thermistors.

The described and illustrated calibration device forms part of the generator and is mounted to the generator housing. However, the device could be used externally and may or may not be connected to the generator. In the latter case, self-calibration may not be possible although the user may, depending on the features of the generator, manually adjust the generator output in response to signals or indications from the calibration device.

Systems within the broader scope of the invention may include systems in which heating energy is delivered to the tissue from a source having a low thermal time constant. Typically, treatment energy can be delivered in pulses of very short duration (typically 0.5 to 100 ms) and without reliance on an intermediary conversion from one kind of energy to another such as a chromophore in laser energy and tissue resistivity in radio frequency energy.

In use, the instrument 16 is passed over the surface of tissue to be cosmetically treated, with the nozzle 29*a* typically being held a few millimeters from the surface of the tissue. The pulse duration and energy levels are chosen so as to form first and second adjacent regions of thermally-modified tissue in the region of the DE Junction. The first, upper region is termed a zone of thermal damage, having a thermal modification which is greater than that of the second, lower region. The thermally damaged zone is thermally modified to an extent that it separates from the second region some days after the delivery of the thermal energy. Following separation of the first damaged region, the epidermis and the upper region of the dermis regenerate naturally.

A benefit of using a diatomic plasma is that it is able to deliver a relatively large amount of energy which causes heating in a short period of time. This enables delivery in discreet pulses of millisecond duration, and is in contrast to heat conduction from a merely hot gas. In the preferred embodiment, energy from 1 Joule to 4 Joules is delivered in a period of 4.5 to 15.4 milliseconds respectively for a nozzle with an exit diameter of 5 millimeters, and delivers from less than 0.5 Joules up to 2 Joules in the same period for a nozzle with an exit diameter of less than 1.5 millimeters. Experiments have shown that useful clinical effects are achieved with yet longer pulses extending to 50 milliseconds, and further analysis shows extension up to 100 milliseconds or more will provide useful effects. In addition, the pulse width may be shortened to deliver the same, or otherwise similar, useful heating energy. Plasma pulses as short as 0.5 milliseconds have been produced with the system described above.

Another benefit is that oxygen is purged from the skin surface by the plasma and flow of inert gas that follows immediately following a plasma pulse. As a result, the oxidative carbonisation that often occurs at the skin surface on application of thermal energy is avoided, leaving a desiccated intact epithelium with minor structural alteration.

This minor structural alteration is nonetheless important in providing yet another benefit of the invention, as it changes the thermal characteristics of the epidermis at higher energy settings. Following a single pass of plasma over the skin surface at an energy setting greater than 2 Joules, the epidermal cells at the basal membrane are heated to a degree that produces vacuolation of the cellular contents. This produces a natural insulator limiting the absorption and depth of penetration of energy from subsequent passes. This is a beneficial safety feature that avoids the risk of excessive damage by inadvertent application of multiple passes to the same site on the skin surface.

Alternatively, when using energy pulses at or below 2 Joules, then the vacuolation is not observed, and the treated skin is still capable of absorbing the thermal energy of a second pass, by changing the energy in the second pass using either a narrow nozzle to focus the plasma or a higher energy setting will have an additive effect. The benefit of using a narrow nozzle embodiment is that the focused energy can be directed onto specific areas of the skin surface such as deeper wrinkles.

For example, if the skin is subjected to two passes of 4 Joules, then the depth of thermal effect is only 10-20% greater than with a single pass of 4 Joules. Alternatively, if the skin is first treated with 2 Joules, then with a second pass of 4 Joules then the effect will be consistent with a single pass with 6 Joules. Part of this benefit also relates to the water content of the skin, particularly the upper layers of the epidermis following pre-treatment with a topical anaesthetic.

Through experimentation with the invention, it has become clear that the depth of effect changes by up to 50% depending on the hydration of the upper layers of the epidermis following application of a topical anaesthetic. Topical anesthetics include a hydrating component, as they rely on hydration of the superficial epidermis for the penetration of the anaesthetic agent through the skin. This changes the absorption of pure thermal energy, whereby a larger proportion of the energy is dissipated in the superficial epidermis, reducing the depth of penetration into the dermis. If no anaesthesia or tumescent subcuticular anaesthesia is employed, then the depth of dermal penetration for a given energy setting can be doubled. A pre-treatment with 2 Joules produces sufficient desiccation of the superficial epidermis, following use of topical anaesthesia, that an equivalent depth of effect can be produced with the second pass to that achieved with no anaesthesia or tumescent subcuticular anaesthesia.

The reason for using a diatomic plasma which delivers a relatively large amount of energy in a short period of time is that the irreversible clinical effects (the thermal modification and thermal damage of the tissue) occur over tissue depths that result in the desired clinical effects, whilst avoiding any undesired clinical effects. If the heating energy is delivered over too long a time, the effects of convection from the skins surface and conduction into the underlying tissue will be such that no significant temperature rise results. On the other hand, if the time is too short, then irreversible effects (such as water vaporising) at or near the skins surface will carry away otherwise useful heating energy.

Figure 9:
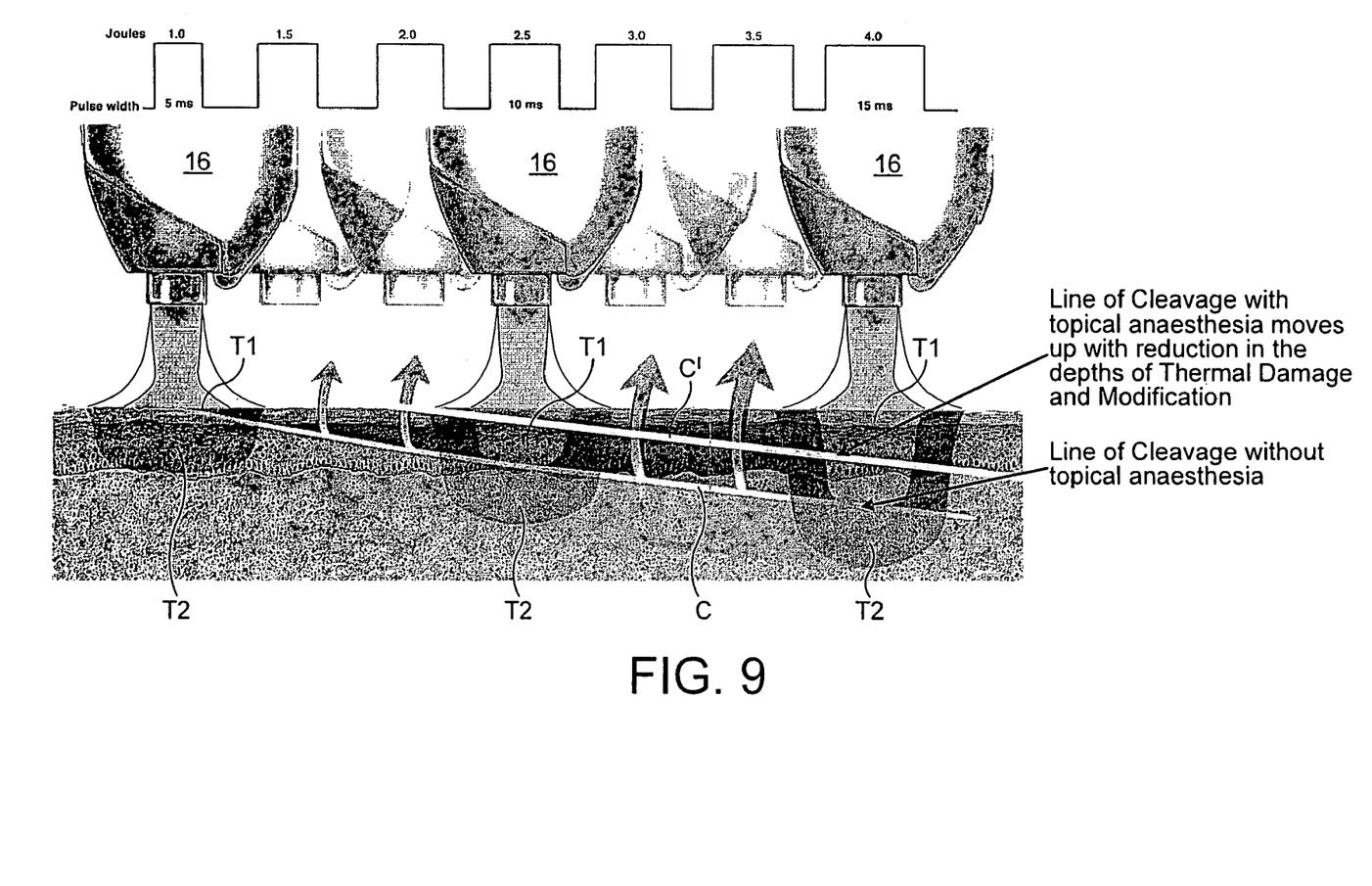
FIG. 9 is a composite diagram showing the regeneration of the reticular architecture of the dermis when using the system of FIGS. 1 to 8 for different pulse widths and energy settings.

FIG. 9 shows the regeneration of the reticular architecture of the dermis for different pulse widths and energy ratings, and illustrates the use of a thermal source with a low thermal time constant. Thus, for an energy setting of 1 Joule, a pulse width of about 5 milliseconds is appropriate, for an energy setting of 2.5 Joules, a pulse width of 10 milliseconds is appropriate, and for an energy setting of 4 Joules, a pulse width of about 15 milliseconds is appropriate. FIG. 9 also shows the two regions of thermal modification T1 and T2, T1 being the upper region of thermal damage, and T2 being the lower region of thermal modification. FIG. 9 also shows the line of cleavage C which develops between these two regions between two and five days after treatment. As is apparent, the depth of effect increases as the energy level and pulse width used for the treatment increases. The dermatologist carrying out the procedure will, therefore, choose the appropriate energy level and pulse width depending on the depth of effect required.

Figure 10:
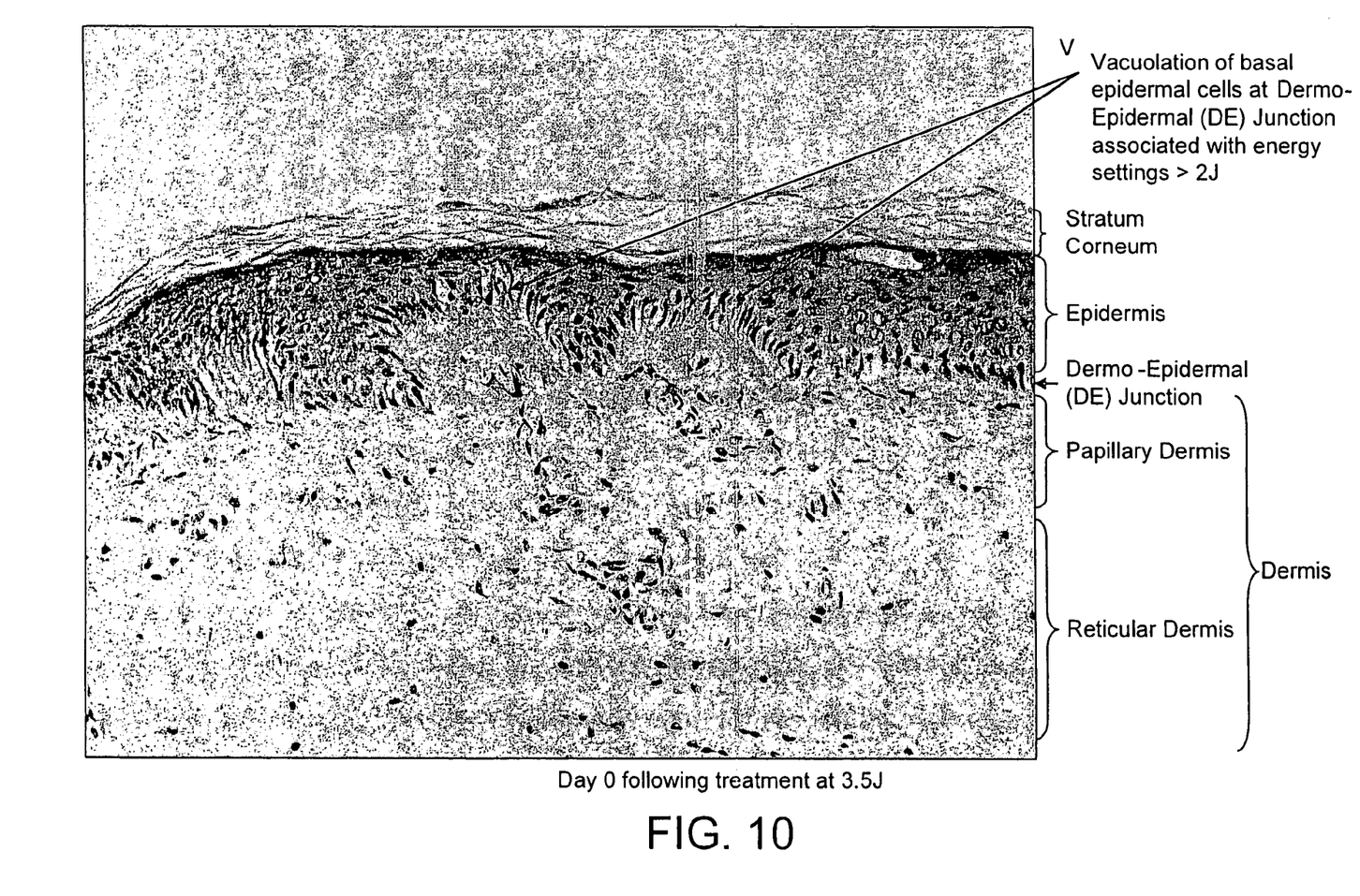
FIGS. 10 to 12 show the process of reticular regeneration at the day of treatment, at four days after treatment, and at ten days after treatment respectively.
Figure 11:
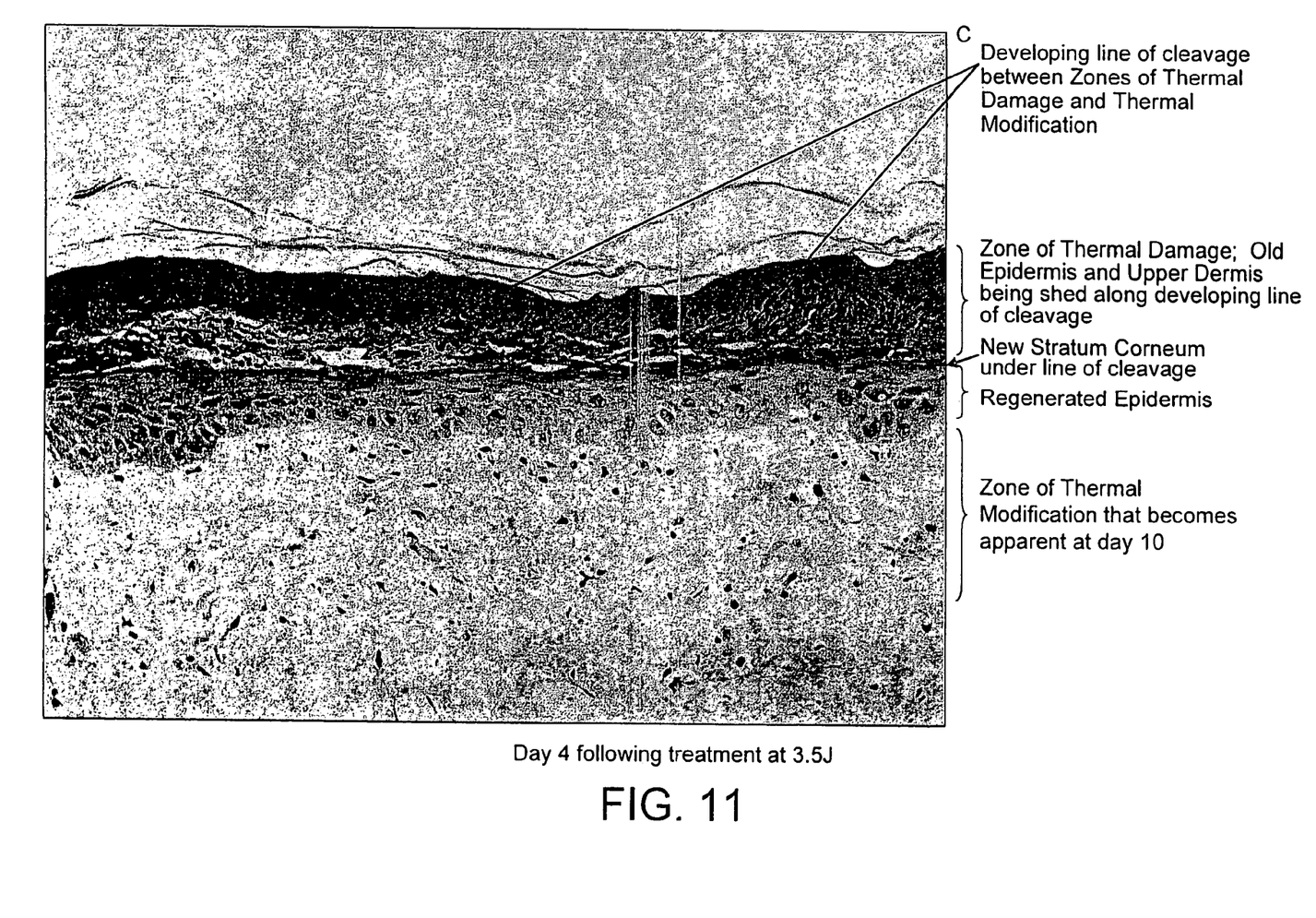
Figure 12:
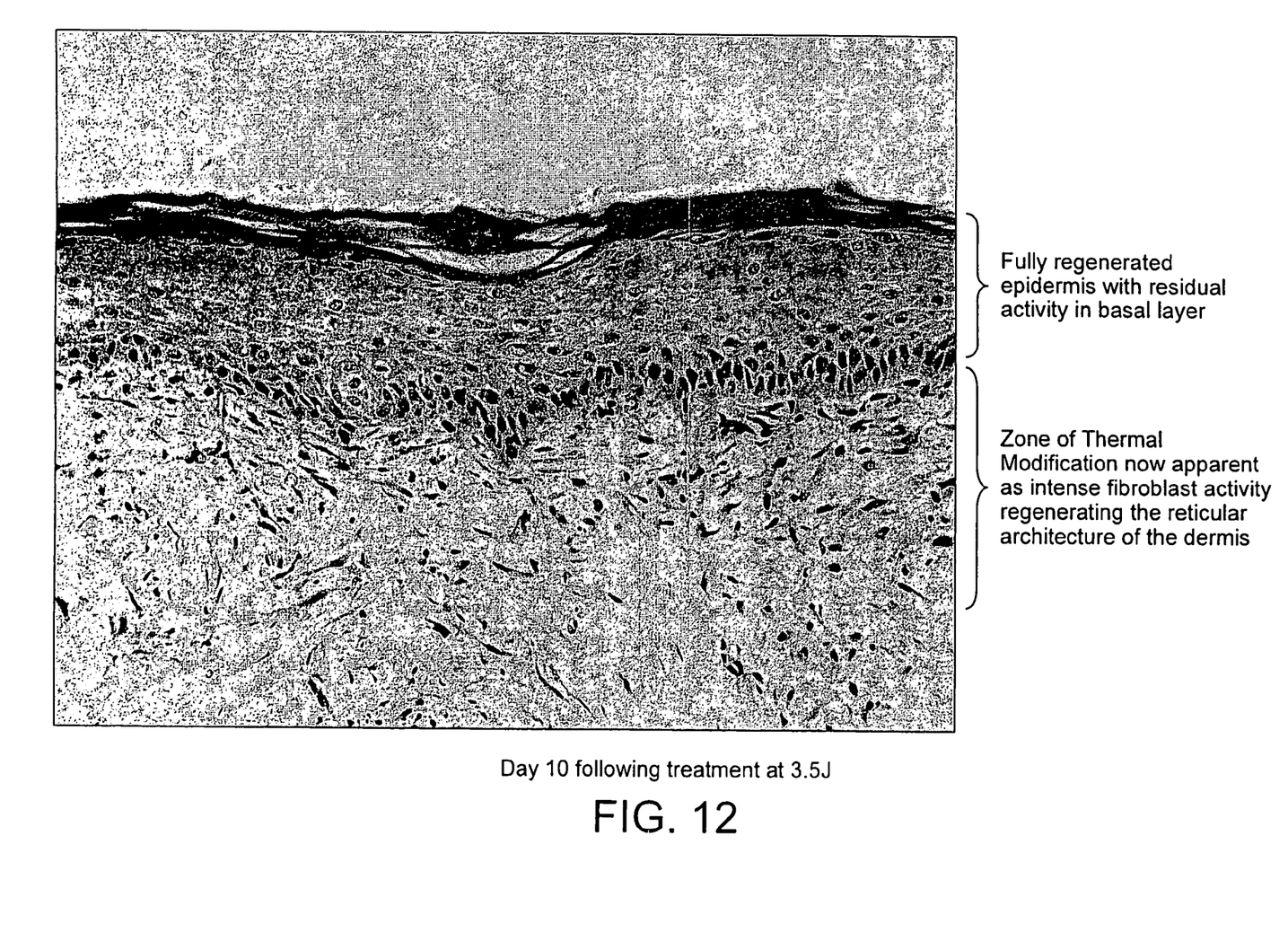

As mentioned above, the use of a topical anaesthetic modifies the effect of the treatment. Thus, as shown in FIG. 9 the line of cleavage C is for treatment without a topical anaesthetic, the equivalent line of cleavage (C1) being higher, owing to a reduction in the depth of thermal damage and modification which results from pre-treatment with a topical anaesthetic. FIGS. 10 to 12 show a typical treatment, and the progress of regeneration of the reticular architecture after the treatment. Thus, FIG. 10 shows the effect of treatment at 3.5 Joules and a pulse width of 13.6 milliseconds immediately following treatment. The Figure shows the dermis (including the reticular dermis and the papillary dermis), the DE Junction, the epidermis and the stratum corneum. Vacuolation of basal epidermal cells at the DE Junction is clearly visible, as indicated by the reference V. FIG. 11 shows the position at day four following treatment at 3.5 Joules, and shows a developing line of cleavage C between the regions T1 and T2 of thermal damage and thermal modification. The region T1 of thermal damage is the old epidermis and the upper dermis, which is in the process of being shed along the developing line of cleavage C. Underneath the line of cleavage C a new stratum corneum and a regenerated epidermis are being developed naturally. FIG. 11 also shows the zone where thermal modification will later become apparent.

FIG. 12 shows the position at day ten following treatment at 3.5 Joules. Here, the epidermis has been fully regenerated with residual activity in the basal layer, and the zone of thermal modification is now apparent, as intense fibroblast activity regenerates the reticular architecture of the dermis.

What is claimed is:

1. A tissue treatment system comprising:
a radio frequency (r.f.) generator;
a treatment instrument connectible to the generator and to
  a source of ionisable gas and operable to produce a
  plasma jet at a nozzle of the instrument when supplied
  with the ionisable gas and energised by the generator;
  and
a calibration device that comprises:
  a target element having a target surface area;
  a transducer arranged to produce an electrical signal
    indicative of a temperature change of the target element within the target surface area;
  a receptacle for locating the nozzle of the instrument in
    juxtaposition with the target surface area whereby, in
    operation of the instrument when the nozzle is in the
    receptacle, the plasma jet is incident upon the target surface area to cause the transducer to generate a calibration signal for adjusting the energy output of the generator; and an output connected to the generator for coupling the calibration signal to the generator;

wherein the generator includes an energy output adjuster for adjusting the r.f. energy output of the generator, the adjuster being configured to adjust the r.f. energy output in response to the calibration signal.

2. A system according to claim 1, wherein the adjuster forms part of a controller which is configured to perform an automatic calibration process in which the generator is operated to feed a predetermined r.f. energy waveform to the instrument to cause generation of a calibrated plasma jet directed at the target surface area of the calibration device, the calibration signal generated as a result of the calibrated jet heating the target element is processed to produce a calibration value which is then compared with a reference value, and the adjuster is operated automatically in response to a deviation of the calibration value from the reference value to set the r.f. energy output for subsequent operation of the system.

3. A system according to claim 2, wherein the predetermined r.f. energy waveform comprises a plurality of pulses of r.f. energy.

4. A system according to claim 3, wherein the calibration value is a function combining the levels of successive pulses which are generated by the transducer and correspond to the pulses of r.f. energy.

5. A system according to claim 1, wherein the target element is a metallic plate and the transducer is in contact with the plate.

6. A system according to claim 5, wherein the transducer has an area greater than the cross-sectional area of the plasma jet when the instrument is operated in its calibration location.

7. A system according to claim 6, wherein the transducer comprises a plurality of temperature sensitive elements distributed in an array.

8. A system according to claim 1, wherein the transducer is arranged to produce an electrical signal representative of a difference in temperature between first and second elements of the transducer.

9. A system according to claim 1, wherein the transducer has a measurement surface and a reference surface, which surfaces are spaced apart, and wherein the transducer is operable to produce an electrical signal which is substantially linearly related to the difference between a temperature sensed at the measurement surface and a temperature sensed simultaneously at the reference surface.

10. A system according to claim 1, wherein the target element comprises a first transducer element, wherein the calibration device has a second transducer element spaced from the first transducer element, and wherein the system is arranged to perform a calibration process during which the temperature existing at the first transducer element is compared with the temperature existing at the second transducer element to produce the electrical signal.

11. A system according to claim 1, wherein the calibration device comprises a calorimeter having a metallic plate forming the target element, a heat sink portion underlying the metallic plate, and a temperature difference sensor located between the metallic plate and the heat sink portion and arranged to produce an electrical output signal indicative of the difference in temperature between the metallic plate and the heat sink portion.

12. A system according to claim 11, wherein the sensor comprises a Peltier device.

13. A system according to claim 1, wherein the generator is operable in a calibration mode to cause a burst of r.f. energy to be delivered to the instrument with a predetermined waveform and duration so as to cause the instrument, when supplied with the ionisable gas, to generate a calibration plasma jet, and wherein the calibration device is arranged automatically to evaluate the electrical signal produced when the calibration plasma jet is incident on the target surface area to generate an adjustment signal for adjusting the energy output of the generator.

14. A system according to claim 13, wherein the calibration device is arranged to evaluate the level of the electrical signal at a predetermined time after commencement of the burst of r.f. energy.

15. A system according to claim 13, wherein the generator is operable to produce the burst as a plurality of pulses and the calibration device is arranged to evaluate the level of the electrical signal after the application of a predetermined number of pulses.

16. A system according to claim 13, wherein the transducer is a temperature difference sensor and the calibration device is arranged to evaluate the level of the electrical signal when it reaches a maximum level.

17. A system according to claim 13, wherein the generator is operable to produce the burst as a succession of pulses, the transducer is a temperature difference sensor, and the calibration device is arranged to evaluate the level of the electrical signal when it reaches a peak level associated with the nth pulse occurring in the succession of pulses, n being a predetermined integer.

18. A system according to claim 1, wherein:
the generator is contained within a generator housing to which the treatment instrument is coupled by a cable for conveying r.f. energy from the generator to the instrument;
the calibration device is in the generator housing and has an associated instrument holder which opens out on a front section of the housing for receiving the instrument and which is shaped to locate the instrument longitudinally and transversely with respect to the target element.

19. A method of calibrating a tissue treatment system which includes a radio frequency (r.f.) generator, a treatment instrument connected to the generator and to a source of ionisable gas, and a calibration device comprising a target element and a temperature sensing transducer, a receptacle for locating a nozzle of the instrument in juxtaposition with a target surface area of the target element at a pre-defined location with respect thereto, and an output coupled to the generator, wherein the method comprises:
placing the treatment instrument in the receptacle;
causing gas to be supplied to the instrument and simultaneously causing a burst of r.f. energy to be delivered to the instrument with a predetermined waveform and duration so as to generate a plasma jet exiting the nozzle and incident upon the target element;
automatically evaluating a calibration signal generated by the calibration device at the output and representative of an output of the transducer resulting from heating of the target element by the plasma jet; and
setting the r.f. energy output level of the generator according to the evaluation of the calibration signal.

* * * * *